(12) United States Patent
Gullberg et al.

(10) Patent No.: US 8,748,603 B2
(45) Date of Patent: Jun. 10, 2014

(54) CRYSTALLINE FORMS OF N-[2-[[(2,3-DIFLUOROPHENYL)METHYL]THIO]-6-{[(1R,2S)-2,3-DIHYDROXY-1-METHYLPROPYL]OXY}-4-PYRIMIDINYL]-1-AZETIDINESULFONAMIDE

(75) Inventors: Britt Anne Ingela Gullberg, Lund (SE); Thomas Peter Larsson, Mölndal (SE); Jeffrey Paul Stonehouse, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 270 days.

(21) Appl. No.: 13/180,900

(22) Filed: Jul. 12, 2011

(65) Prior Publication Data

US 2012/0015927 A1    Jan. 19, 2012

Related U.S. Application Data

(60) Provisional application No. 61/363,726, filed on Jul. 13, 2010.

(51) Int. Cl.
| | | |
|---|---|---|
| *C07D 403/12* | (2006.01) | |
| *A61K 31/506* | (2006.01) | |
| *A61P 19/02* | (2006.01) | |
| *A61P 11/06* | (2006.01) | |

(52) U.S. Cl.
USPC ............ 544/310; 544/311; 544/317; 514/269

(58) Field of Classification Search
USPC .......................... 544/310, 311, 317; 514/269
See application file for complete search history.

(56) References Cited

U.S. PATENT DOCUMENTS

| 2006/0025432 | A1 | 2/2006 | Ebden et al. |
|---|---|---|---|
| 2008/0096860 | A1 | 4/2008 | Cheshire et al. |
| 2010/0016275 | A1 | 1/2010 | Meghani et al. |
| 2010/0063079 | A1 | 3/2010 | Ebden et al. |
| 2011/0124919 | A1 | 5/2011 | Ernst et al. |
| 2012/0157431 | A1 | 6/2012 | Cheshire et al. |
| 2013/0012490 | A1 | 1/2013 | Cheshire et al. |
| 2013/0040926 | A1 | 2/2013 | Connolly et al. |
| 2013/0203991 | A1 | 8/2013 | Cheshire et al. |

FOREIGN PATENT DOCUMENTS

| WO | 2004/011443 | 2/2004 |
|---|---|---|
| WO | 2006/024823 | 3/2006 |
| WO | 2010/007427 | 1/2010 |

OTHER PUBLICATIONS

Dermer et al., Bio/Technology, 1994, 12:320.*
Freshney et al.,Culture of Animal Cells, A Manual of Basic Technique, Alan R. Liss, Inc., 1983, New York, p. 4.*
Golub et al., Science, 286, 531-537, 1999.*
Rostene et al., Nature Reviews Neuroscience, 8, 895-904, 2007.*
Raman et al., Cancer Letters, 256, 137-165, 2007.*
Cecil Textbook of Medicine, edited by Bennet, J.C., and Plum F., 20th edition,vol. 1, 1004-101 O, 1996.*
Caira et al., "Crystalline Polymorphism of Organic Compounds," Topics in Current Chemistry, 198:163-208 (1998).

* cited by examiner

*Primary Examiner* — Venkataraman Balasubramanian
(74) *Attorney, Agent, or Firm* — Morgan, Lewis & Bockius LLP

(57) ABSTRACT

There is provided crystalline forms of N-[2-[[(2,3-difluorophenyl)methyl]thio]-6-{[(1R,2S)-2,3-dihydroxy-1-methylpropyl]oxy}-4-pyrimidinyl]1-azetidinesulfon-amide anhydrate. Such compounds/forms may be useful in the treatment of a disease/condition in which modulation of chemokine receptor activity is beneficial.

7 Claims, 3 Drawing Sheets

CRYSTALLINE FORMS OF N-[2-[[(2,3-DIFLUOROPHENYL)METHYL]THIO]-6-{[(1R,2S)-2,3-DIHYDROXY-1-METHYLPROPYL]OXY}-4-PYRIMIDINYL]-1-AZETIDINESULFONAMIDE

CROSS-REFERENCE TO RETATED APPLICATIONS

This application claims the benefit under 35 U.S.C. §119(e) of U.S. Application No. 61/363,726 filed on Jul. 13, 2010, which is incorporated herein by reference in its entirely.

This invention relates to new solid state forms of a drug, to pharmaceutical compositions containing them, and to processes for obtaining them.

In the formulation of drug compositions, it is desirable for the drug substance to be in a form in which it can be conveniently handled and processed. This is of importance, not only from the point of view of obtaining a commercially viable manufacturing process, but also from the point of view of subsequent manufacture of pharmaceutical formulations comprising the active compound.

Chemical stability, solid state stability, and "shelf life" of the active ingredients are also very important factors. The drug substance, and compositions containing it, should be capable of being effectively stored, without exhibiting a significant change in the active component's physico-chemical characteristics (e.g. its chemical composition, density, hygroscopicity and solubility).

Moreover, it is also desirable to be able to provide drug in a form which is as chemically pure as possible.

Amorphous, or semi-amorphous materials may present significant problems in this regard. For example, such materials are typically difficult to handle and to formulate, provide for unreliable solubility, and are often found to be unstable and chemically impure.

The skilled person will appreciate that, if a drug can be readily obtained in a stable crystalline form, the above problems may be solved.

Furthermore, crystalline drug compounds have been shown to provide more reliable and reproducible plasma concentration profiles following administration to a patient.

Thus, in the manufacture of commercially viable, and pharmaceutically acceptable, drug compositions, it is desirable, wherever possible, to provide drug in a substantially crystalline, and stable, form.

It is to be noted, however, that this goal is not always achievable. Indeed, typically, it is not possible to predict, from molecular structure alone, what the crystallisation behaviour of a compound will be. This can usually only be determined empirically.

International patent application WO 2006/024823 discloses a number of pyrimidine sulphonamide derivatives as chemokine receptor modulators, including the specific compound N-[2-[[(2,3-difluorophenyl)methyl]thio]-6-{[(1R, 2S)-2,3-dihydroxy-1-methylpropyl]oxy}-4-pyrimidinyl]-1-azetidinesulfonamide (Example 47):

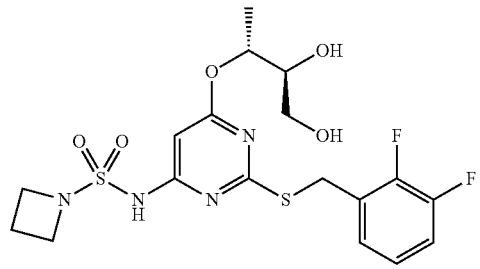 [SMILES: C[C@@H](Oc1cc(NS(=O)(=O)N2CCC2)nc(SCc2cccc(F)c2F)n1)[C@@H](O)CO]

also referred to herein as Compound I.

WO 2006/024823 discloses a process for preparing Compound I, but does not disclose any specific information regarding crystalline forms of that compound.

We have now found that it is possible to produce stable, crystalline forms of Compound I, or a pharmaceutically acceptable salt thereof, which crystalline forms may be referred to herein at the "compounds of the invention".

According to an aspect of the invention, there is provided a substantially crystalline form of Compound I, or a pharmaceutically acceptable salt thereof (for the avoidance of doubt, these are "compounds of the invention").

In another aspect of the invention, there is provided a crystalline form of Compound I, or a pharmaceutically acceptable salt thereof.

According to a further aspect of the invention, there is provided a substantially crystalline anhydrate form of Compound I (for the avoidance of doubt, these are "compounds of the invention"). In one aspect, Compound I is not in the form of a salt. It is further preferred that it is not in the form of a solvate, i.e. it is an "ansolvate". Hence, the term "anhydrate" encompasses "ansolvate".

We have found that Compound I may be obtained in forms that are substantially crystalline in nature. Although it is possible to produce Compound I in forms that are greater than about 90%, such as greater that about 95%, crystalline (e.g. greater than about 98% crystalline and, particularly, 100%, or nearly 100%, crystalline), by "substantially crystalline" we include greater than about 60%, in another aspect greater than about 75%, and in yet another aspect greater than about 80% (such as about 90%) crystalline. The degree (%) of crystallinity may be determined by the skilled person using X-ray powder diffraction (XRPD). Other techniques, such as solid state NMR, FT-IR, Raman spectroscopy, differential scanning calorimetry (DSC) microcalorimetry, and calculations of the true density, may also be used.

Suitable a crystalline modification of a compound according to the invention is substantially free from other crystalline modifications of the compound. Suitably, a described crystalline modification of a compound of formula I includes less than, for example 20%, 15%, 10%, 5%, 3% or particularly, less then 1% by weight of other crystalline forms of that compound.

It is stated hereinbefore that Compound I may be produced in a crystalline form that is an anhydrate. By this we mean that the crystalline form contains less than 10% of (a) hydrate form(s) (e.g. a monohydrate) of Compound I.

Two preferred anhydrate crystalline forms of Compound I may be characterised by an X-ray powder diffraction pattern, using X-rays of wavelength 1.5418 Å, comprising the following characteristic crystalline peaks with approximate 2-Theta values (in degrees) as well as an indication of the relative intensity of those peaks in brackets, where a percentage relative intensity of approximately 25-100% is termed "vs", approximately 10-25% is termed "s", approximately 3-10% is termed "m" and approximately 1-3% is termed "w":

Form A: characteristic crystalline peaks with at least one 2-Theta values (in degrees) of around (i.e. at about or at approximately) 14.8, 17.8 and/or 24.1. In one aspect, characteristic crystalline peaks with at least one 2-Theta values (in degrees) of 14.8, 17.8 and/or 24.1. In another aspect, all of these peaks are present. In yet another aspect, also comprising at least one further crystalline peaks with a 2-Theta value (in degrees) of around (i.e. at about or at approximately) 16.3, 15.5, 11.4, 9.9, 13.1 and/or 4.4. In yet another aspect, all of the aforementioned peaks are present. In yet another aspect, also comprising at least one further crystalline peaks with a 2-Theta value (in degrees) of 16.3, 15.5, 11.4, 9.9, 13.1 and/or 4.4. In another aspect, all of the aforementioned peaks are present.

In another aspect, form A has characteristic crystalline peaks with at least one 2-Theta values (in degrees) of around (i.e. at about or at approximately) 14.8 (s), 17.8 (vs) and/or 24.1 (vs). In one aspect, all of these peaks are present. In another aspect, also comprising at least one further crystalline peaks with a 2-Theta value (in degrees) of around (i.e. at about or at approximately) 16.3 (s), 15.5 (s), 11.4 (vs), 9.9 (vs), 13.1 (vs) and/or 4.4 (vs). In another aspect, all of these peaks are present. In one aspect, the form comprises all the characteristic peaks (e.g. with the indicated relative intensity) as shown by Example 1 hereinafter and hence the form may be characterised by the X-ray powder diffractogram that is essentially that shown in FIG. 1.

Form D: characteristic crystalline peaks with at least one 2-Theta values (in degrees) of around (i.e. at about or at approximately) 12.9, 18.0 and/or 21.0. In one aspect, all of these peaks are present. In another aspect, also comprising at least one further crystalline peak with a 2-Theta value (in degrees) of around (i.e. at about or at approximately) 25.1, 25.3, 27.0 and/or 29.1. In yet another aspect, all of these peaks are present.

In another aspect, form D has characteristic crystalline peaks with at least one 2-Theta values (in degrees) of around (i.e. at about or at approximately) 12.9 (vs), 18.0 (vs) and/or 21.0 (s). In one aspect, all of these peaks are present. In another aspect, also comprising at least one further crystalline peak with a 2-Theta value (in degrees) of around (i.e. at about or at approximately) 25.1 (s), 25.3 (s), 27.0 (s) and/or 29.1 (s). In yet another aspect, all of these peaks listed for form D are present. In another aspect, the form comprises all the characteristic peaks (e.g. with the indicated relative intensity) as shown by Example 2 hereinafter and hence the form may be characterised by the X-ray powder diffractogram that is essentially that shown in FIG. 2.

In another aspect form D is characterised by a powder X-ray diffraction pattern, measured using a wavelength of X-rays 1.5418 Å, comprising at least 1 crystalline peak with a 2-Theta value (in degrees) of 21.0, 28.8 and/or 29.1.

In another aspect form D is characterised by a powder X-ray diffraction pattern, measured using a wavelength of X-rays 1.5418 Å, comprising at least 2 crystalline peaks with a 2-Theta value (in degrees) of 21.0, 28.8 and/or 29.1.

In another aspect form D is characterised by a powder X-ray diffraction pattern, measured using a wavelength of X-rays 1.5418 Å, comprising at least 3 crystalline peaks with a 2-Theta value (in degrees) of 21.0, 28.8 and/or 29.1.

In another aspect form D is characterised by a powder X-ray diffraction pattern, measured using a wavelength of X-rays 1.5418 Å, comprising a further crystalline peak with a 2-Theta value (in degrees) selected from of 12.9 and 18.0.

In another aspect form D is characterised by a powder X-ray diffraction pattern, measured using a wavelength of X-rays 1.5418 Å, comprising crystalline peaks with a 2-Theta value (in degrees) of 12.9, 13.1, 18.0, 21.0, 22.5, 25.1, 25.3, 28.8, 29.1 and 30.4.

In one aspect, compounds of the invention are substantially crystallographically pure. By "substantially crystallographically pure" we include a crystalline form of Compound I anhydrate, as far as can be judged by X-ray Powder Diffraction (XRPD) measurements, that contains less than about 5%, in another aspect less than about 3% and in yet another aspect less than about 1% of other crystalline forms of the Compound I (whether it is another anhydrate form or otherwise, and as judged by the presence of XRPD peaks from such other crystalline forms).

DSC analysis shows Form D has an onset of melting at 152.7° C. The DSC thermogram is depicted in FIG. 3. In one aspect the invention relates to a crystalline form of the compound of formula 1 with a melting point of about 152.7° C. (onset).

We have found that, for certain anhydrates of Compound I, solvent drying (during the crystallisation process) is not necessary to ensure formation. However, to ensure that anhydrate is produced, the solvent from which the crystallisation occurs may be dried, either before or during the crystallisation process, in order to reduce the water content below a critical level, which should preferably not be exceeded during the crystallisation. Solvent may be dried during the crystallisation process, for example by decreasing the water content of a mixture of the compound to be crystallised and an appropriate organic solvent/aqueous solvent system (e.g. by increasing the amount of organic solvent that is present and/or removal of water by formation of an azeotrope, with successive distillations).

Hence, the anhydrate of Compound I may be produced by crystallisation from a solvent system which is substantially free of water.

By "substantially free of water", we include that the water content in the solvent system is below that which will result in the formation of, at most, 10% monohydrate, for any particular solvent system and set of crystallisation conditions.

Crystalline Form D of Compound I anhydrate may be prepared by suspension of Compound I (e.g. in amorphous form or in a different crystalline form, such as the Form A) in a solvent system. There is therefore provided a crystalline form obtainable by such a (crystallisation) conversion process. The skilled person will understand that a suspension process is essentially a "slurrying" process or a process that involves at least partial (but not complete) dissolution in a solvent system.

In an aspect of the invention therefore, there is provided the conversion of one crystalline form (e.g. one anhydrate form) of Compound I to another. In particular the Form A (also referred to herein as the A-form) may be converted to the Form D (also referred to herein as the D-form). Again, there is therefore provided a crystalline form obtainable by such a (crystallisation) conversion process.

In order to obtain the D-form, the A-form may be suspended or slurried (or at least partially dissolved) in a solvent system that does not promote the formation of a solvate form of Compound I.

The terms "suspended" and "slurried" (or "partially dissolved") are well understood by the skilled person. For instance to form a suspension or slurry, an excess of the solid substance, relative to the solubility in the solvent, is added such that there is (undissolved) solid in the solvent system throughout the "suspension" or "slurrying" procedure. Hence why it is also referred to herein as "partial dissolution".

Preferred solvent systems employed to obtain the D-form by suspension or slurrying (i.e. to achieve the conversion of e.g. the amorphous Compound I or the A-form, to the D-form) include any suitable solvent (also referred to herein as "the suspension solvent"), or mixture of solvents, that do not result in the formation of a solvate of Compound I. Preferred solvent systems may include those in which the Compound I is only partially (or is at least partially) soluble. In one aspect, the solvent system comprises (or, in another aspect, consists essentially of) organic solvents that are polar, e.g. alcohols (such as lower alkyl alcohols, e.g. a $C_{1-6}$ alcohol). In another aspect, the solvent system comprises (or, in another aspect, consists essentially of) ethanol or, especially, methanol. Hence, the aforementioned polar organic solvents are the particularly preferred suspension solvents employed in the solvent system (and in another aspect, the solvent system consists primarily or essentially of such suspension solvents). In one aspect, the suspension solvent (e.g. alcohol, such as methanol) constitutes at least 90% w/w (e.g. at least 95%, such as about 100%) of the total solvent system that is employed to obtain the D-form. That is, the suspension solvent may contain up to 10% w/w (e.g. up to 5%, or about 0%) of other (undesired or less desired) solvents.

The phase conversion in the solvent system (including the suspension solvent, as hereinbefore described) to obtain the D-form may take up to a period of weeks (e.g. six weeks; see the Example hereinafter), but the length of time may be reduced depending on the temperature of the process (or it may take longer if performed at lower temperatures), etc. However, the skilled person can easily determine the length of time taken for conversion to the D-form. Furthermore, the D-form may be obtained by seeding, for example as described hereinafter.

The A-form of Compound I may be crystallised from the amorphous form of Compound I in a mixture containing a certain solvent (e.g. acetonitrile), an inorganic acid (e.g. phosphoric acid) and water, which mixture may be heated and then cooled to promote crystallisation, as described hereinafter (see e.g. Example 2).

The A-form of Compound I may be crystallised from N-[2-[[(2,3-difluorophenyl)methyl]thio]-6-[(1R)-1-[(4S)-2,2-dimethyl-1,3-dioxolan-4-yl]ethoxy]-4-pyrimidinyl]-1-azetidinesulfonamide in a mixture containing a certain solvent (e.g. acetonitrile), an inorganic acid (e.g. phosphoric acid) and water, which mixture may be heated and then cooled to promote crystallisation, as described hereinafter (see e.g. Example 2).

Crystallisations described herein may also be promoted by the addition of seed crystals (once available).

For instance, the D-form may also be prepared by seeding, using the following procedure: dissolving Compound I (e.g. one 'weight' %) in a solvent (such as an alcohol, e.g. isopropanol; e.g. 30 relative volumes); stirring at elevated temperature (e.g. 70° C.) for instance for a period of time (which may be several hours) to achieve the full dissolution; continuing stirring at elevated temperature (e.g. 55° C.; i.e. at a temperature lower than that required to achieve dissolution) for a period of time e.g. several hours (e.g. overnight); seeding with Form D of Compound I (e.g. 0.1 weight %); cooling to a lower temperature (e.g. 20° C.); and filtering to yield the D-form.

Alternatively, the D-form may also be prepared by seeding, using the following procedure: dissolving Compound I (e.g. one relative 'weight' %) in a solvent (such as an alcohol, e.g. ethanol; e.g. 15 relative volumes); stirring at elevated temperature (e.g. 65° C.) for instance for a period of time (which may be several hours) to achieve the full dissolution; continuing stirring at elevated temperature (e.g. 55° C.; i.e. at a temperature lower than that required to achieve dissolution) for a period of time e.g. several hours (e.g. overnight); seeding with Form D of Compound I (e.g. 0.1 weight %); cooling to a lower temperature (e.g. 20° C.); and filtering to yield the D-form.

In order to ensure that crystalline forms as described herein are prepared in the absence of other crystalline forms, crystallisations may be carried out by seeding with nuclei and/or seed crystals of the desired crystalline form in the absence of nuclei and/or seed crystals of other crystalline forms.

The skilled person will appreciate that the concentration in solution of the compound that is to be crystallised, and the solvent system that is used, may influence crystallisation temperatures and crystallisation times.

Different crystalline forms may have different solubility in different organic solvents at any given temperature. In this respect, above-mentioned, or other, solvents may be employed as "antisolvents" (i.e. a solvent in which compounds of the invention are poorly soluble, but which is miscible with another solvent, in which compounds of the invention are more soluble), and may thus aid the crystallisation process.

As may be appreciated by the skilled person, the crystalline form that is obtained depends upon both the kinetics and the thermodynamics of the crystallisation process. Under certain thermodynamic conditions (solvent system, temperature, pressure and concentration of the compound of the invention), one crystalline form may be more stable than another (or indeed any other). However, other crystalline forms that may have, in comparison, a relatively low thermodynamic stability, may be kinetically-favoured. Thus, in addition, kinetic factors, such as time, impurity profile, agitation, the presence of seeds, etc. may also influence which forms appear. Thus, the procedures discussed herein may be adapted by the skilled person as appropriate in order to obtain the particular crystalline form of Compound I (e.g. the A-form or D-form).

Further, drying temperature and drying time may affect the solid state properties and/or the solid state form of compounds of the invention. For example, dehydration may occur at low humidity and/or elevated temperatures and/or reduced pressure. Hence, the crystalline anhydrates of compounds of the invention may also be formed by dehydration of a hydrate.

As stated hereinbefore, preferred compounds of the invention may also be characterised by a powder X-ray diffraction pattern that is essentially according to that shown in FIG. 1 or FIG. 2 attached hereto and/or as tabulated in Table 1 or Table 2 hereinafter (see Examples 1 and 2). The skilled person will appreciate that a form of a crystalline anhydrate form of Compound I shows "essentially" the same powder X-ray diffraction pattern as another when it was clear to that skilled person from the respective patterns (i.e. the relative spacing of the peaks, allowing for experimental error, such as preferred orientation of the sample and respective instrument settings (e.g. apparatus type, standardization and/or calibration)) that the same crystalline form has been formed. Thus, there may be some experimental error for °2 Theta values as may be specified herein (e.g. a variation of up ±0.5° 2-theta).

We have found that the compounds of the invention have a surprisingly improved physical and/or chemical stability when compared with other forms of Compound I that may have previously been prepared.

The term "stable" as defined herein includes chemical stability and solid state stability.

By "chemical stability", we include that the compound can be stored in an isolated solid form, or in the form of a solid formulation in which it may be provided in admixture with pharmaceutically acceptable carriers, diluents or adjuvants, under normal storage conditions, with an insignificant degree of chemical degradation or decomposition.

By "solid state stability", we include that the compound can be stored in an isolated solid form, or in the form of a solid formulation in which it may be provided in admixture with pharmaceutically acceptable carriers, diluents or adjuvants, under normal storage conditions, with an insignificant degree of solid state transformation (e.g. crystallisation, recrystallisation, loss of crystallinity, solid state phase transition, hydration, dehydration, solvatisation or desolvatisation).

Examples of "normal storage conditions" include temperatures of between minus 80 and plus 50° C. (in one aspect between 0 and 40° C. and in another aspect at ambient temperature, such as between 15 and 30° C.), pressures of between 0.1 and 2 bars (in one aspect at atmospheric pressure), and/or exposure to 460 lux of UV/visible light, for prolonged periods (i.e. greater than or equal to six months). Under such conditions, compounds of the invention may be found to be less than about 15%, in one aspect less than about 10%, and in another aspect less than about 5%, chemically degraded/decomposed, or solid-state transformed, as appropriate. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

The term "normal storage conditions" may also include relative humidities of between 5 and 95% (in one aspect 10 to 60%). However, in the case of certain crystalline forms according to the invention, changes in conformation or crystal structure by hydration and/or dehydration may occur as a result of prolonged exposure to certain extremes of relative humidities, at normal temperatures/pressures.

The preparation and characterisation of compounds of the invention are described hereinafter. Different crystalline forms of the compounds of the invention may be readily characterised using X-ray powder diffraction (XRPD) methods, for example as described hereinafter.

Compounds of the invention may be isolated using techniques which are well known to those skilled in the art, for example decanting, filtering and/or centrifuging.

We have found that, by employing the crystallisation or conversion processes described herein, it is possible to produce compounds of the invention with a high chemical purity.

When compounds of the invention are prepared as described herein, the resultant compound is in a form which has improved chemical and solid state stability, as mentioned hereinbefore, as well as improved solubility and hygroscopicity profiles when compared to other previously known forms.

Although in one aspect, compounds of the invention (i.e. the crystalline forms) are not in the form of salts, salts that may be mentioned include acid addition salts and base addition salts.

Pharmaceutical Preparations and Medical Use

The compounds of the invention are useful because they possess pharmacological activity. They are therefore indicated as pharmaceuticals.

In particular, the compounds of the invention find utility in the treatment of diseases/conditions in which modulation of chemokine receptor activity, especially CXCR2, is beneficial.

The term "modulation" may refer to any measurable reduction and/or prevention of the relevant activity (chemokine receptor activity). The modulation of chemokine receptor activity may be measured by comparing the chemokine receptor activity in a sample containing a compound of the invention and in a sample in the absence of a compound of the invention (as would be apparent to those skilled in the art). The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

The compound of formula (1) or pharmaceutically acceptable salts may be used in the treatment (therapeutic or prophylactic) of conditions/diseases in human and non-human animals which are exacerbated or caused by excessive or unregulated production of chemokines. Examples of such conditions/diseases include (each taken independently):

(1) the respiratory tract—obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; bronchiectasis; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) bone and joints—rheumatoid arthritis, seronegative spondyloarthropathies (including ankylosing spondylitis, psoriatic arthritis and Reiter's disease), Behchet's disease, Sjogren's syndrome and systemic sclerosis;

(3) skin—psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) gastrointestinal tract—Coeliac disease, proctitis, eosinopilic gastro-enteritis, mastocytosis, Crohn's disease, ulcerative colitis, indeterminate colitis, microscopic colitis, inflammatory bowel disease, irritable bowel syndrome, non-inflammatory diarrhea, food-related allergies which have effects remote from the gut, e.g., migraine, rhinitis and eczema;

(5) central and peripheral nervous system—Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal disorders, e.g. tropical spastic paraparesis, and stiff-man syndrome: paraneoplastic syndromes, e.g. cerebellar degeneration and encephalomyelitis; CNS trauma; migraine; and stroke.

(6) other tissues and systemic disease—atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) allograft rejection—acute and chronic following, for example, transplantation of kidney, heart, liver, lung, bone marrow, skin and cornea; and chronic graft versus host disease;

(8) cancers—especially non-small cell lung cancer (NSCLC), malignant melanoma, prostate cancer and squamous sarcoma, and tumour metastasis, non melanoma skin cancer and chemoprevention metastases;

(9) diseases—in which angiogenesis is associated with raised CXCR2 chemokine levels (e.g. NSCLC, diabetic retinopathy);

(10) cystic fibrosis;

(11) burn wounds & chronic skin ulcers;

(12) reproductive diseases—for example disorders of ovulation, menstruation and implantation, pre-term labour, endometriosis;

(13) re-perfusion injury—in the heart, brain, peripheral limbs and other organs, inhibition of atherosclerosis.

Thus, the present invention provides a compound of formula (1), or a pharmaceutically-acceptable salt as hereinbefore defined for use in therapy.

The compounds of the invention may be used to treat diseases in which the chemokine receptor is the CXCR2 receptor.

Particular conditions which may be treated with the compounds of the invention are cancer, diseases in which angiogenesis is associated with raised CXCR2 chemokine levels, and inflammatory diseases such as asthma, allergic rhinitis, COPD, bronchiectasis, rheumatoid arthritis, psoriasis, inflammatory bowel diseases, osteoarthritis or osteoporosis.

In another aspect particular conditions which may be treated with the compounds of the invention are asthma, COPD and bronchiectasis.

As a further aspect of the present invention, the compound of formula (1) may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma). In particular, the compounds are indicated for use in the treatment of neurodegenerative disorders or demyelinating disease in mammals including man More particularly, the compounds are indicated for use in the treatment of multiple sclerosis. The compounds are also indicated to be useful in the treatment of pain, rheumatoid arthritis, osteoarthritis, stroke, atherosclerosis and pulmonary arterial hypertension.

In a further aspect, the present invention provides a compound of formula (1), or a pharmaceutically acceptable salt, as hereinbefore defined for use as a medicament.

In a still further aspect, the present invention provides the use of a compound of formula (1), or a pharmaceutically acceptable salt, as hereinbefore defined for use as a medicament for the treatment of human diseases or conditions in which modulation of chemokine receptor activity is beneficial.

In a still further aspect, the present invention provides the use of a compound of formula (1), or a pharmaceutically acceptable salt, as hereinbefore defined for use as a medicament for the treatment of asthma, allergic rhinitis, cancer, COPD, rheumatoid arthritis, psoriasis, inflammatory bowel diseases, osteoarthritis or osteoporosis.

In a further aspect, the present invention provides the use of a compound of formula (1), or a pharmaceutically acceptable salt, as hereinbefore defined in the manufacture of a medicament for use in therapy.

In a still further aspect, the present invention provides the use of a compound of formula (1), or a pharmaceutically acceptable salt, as hereinbefore defined in the manufacture of a medicament for the treatment of human diseases or conditions in which modulation of chemokine receptor activity is beneficial.

In a still further aspect, the present invention provides the use of a compound of formula (1), or a pharmaceutically acceptable salt, as hereinbefore defined in the manufacture of a medicament for the treatment of asthma, allergic rhinitis, cancer, COPD, rheumatoid arthritis, psoriasis, inflammatory bowel diseases, osteoarthritis or osteoporosis.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula, or a pharmaceutically acceptable salt, as hereinbefore defined.

The invention also provides a method of treating an inflammatory disease, especially asthma, allergic rhinitis, COPD, rheumatoid arthritis, psoriasis, inflammatory bowel diseases, osteoarthritis or osteoporosis, in a patient suffering from, or at risk of, said disease, which comprises administering to the patient a therapeutically effective amount of a compound of formula (1), or a pharmaceutically acceptable salt, as hereinbefore defined.

More specifically, the compounds of the invention may be useful in the treatment of asthma, allergic rhinitis, COPD, inflammatory bowel disease, irritable bowel syndrome, osteoarthritis, osteoporosis, rheumatoid arthritis, psoriasis or cancer.

Compounds of the invention are indicated both in the therapeutic and/or prophylactic treatment of the above-mentioned conditions.

The term "atherosclerosis" will be understood by those skilled in the art to include any disease characterised by cholesterol accumulation, foam cell formation, inflammation and cell proliferation in a blood vessel, especially an artery wall.

According to a further aspect of the invention there is provided a method of treatment of a disease/condition in which modulation of chemokine receptor activity is beneficial (e.g. a specific disease/condition mentioned herein), which method comprises the administration of a compound of the invention to a patient in need of such treatment.

"Patients" include mammalian (including human) patients. Hence, the method of treatment discussed above may include the treatment of a human or animal body.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form. For instance, the pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. In one aspect, the compounds of the invention are administered orally.

Compounds of the invention may be administered alone, but are in one aspect of the invention are administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent and/or carrier. Such formulations may be administered as described hereinbefore. The compound of the invention (i.e. the crystalline form) that is the active ingredient of the pharmaceutical formulation may be milled or ground into smaller particles.

Depending on e.g. potency and physical characteristics of the compound of the invention (i.e. active ingredient), pharmaceutical formulations that may be mentioned include those in which the active ingredient (i.e. the compound of the invention) is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined, with a pharmaceutically-acceptable adjuvant, diluent or carrier.

Compounds of the invention may also be combined with other therapeutic agents, for instance those that are also useful in the treatment of a disease/condition in which modulation of chemokine receptor activity is beneficial (e.g. those diseases/conditions mentioned herein). Compounds of the invention may also be combined with other therapies.

According to a further aspect of the invention, there is provided a combination product comprising:
(A) a compound of the invention, as hereinbefore defined; and
(B) another therapeutic agent that is useful in the treatment of a disease/condition in which modulation of chemokine receptor activity is beneficial (e.g. a disease/condition described herein),
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent that is useful in the treatment of a disease/condition in which modulation of chemokine receptor activity is beneficial, and a pharmaceutically-acceptable adjuvant, diluent or carrier; and
(2) a kit of parts comprising components:
(a) a pharmaceutical formulation including a compound of the invention, as hereinbefore defined, in admixture with a pharmaceutically-acceptable adjuvant, diluent or carrier; and
(b) a pharmaceutical formulation including another therapeutic agent that is useful in the treatment of a disease/condition in which modulation of chemokine receptor activity is beneficial in admixture with a pharmaceutically-acceptable adjuvant, diluent or carrier, which components (a) and (b) are each provided in a form that is suitable for administration in conjunction with the other.

The invention further provides a process for the preparation of a combination product as hereinbefore defined, which process comprises bringing into association a compound of the invention, as hereinbefore defined, with the other therapeutic agent that is useful in the treatment of cancer and/or a proliferative disease, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Depending on the disorder, and the patient to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Wherever the word "about" is employed herein, for example in the context of amounts (e.g. values, weights, volumes, moles), temperatures, degrees of crystallinity, degrees of degradation, degrees of purity, degrees of dissolution and doses of active ingredients, it will be appreciated that such variables are approximate and as such may vary by ±10%, for example ±5%, ±2%, or ±1% from the numbers specified herein.

Compounds of the invention have the advantage that they are in a form which provides for improved ease of handling, and may be produced in forms which have improved chemical and solid state stability when compared to forms prepared previously. Thus, compounds may be stable when stored over prolonged periods. In particular, the D-form (see Example 2 hereinafter) may have improved thermodynamic stability, compared to forms of Compound I previously prepared.

Compounds of the invention also have improved solubility and hygroscopicity profiles when compared to previously-available forms.

Compounds of the invention may also have the advantage that they may be prepared in good yields, in a higher purity, in less time, more conveniently, and at a lower cost, than forms prepared previously.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, known compounds (e.g. previously known forms of Compound I), whether for use in the above-stated indications or otherwise.

The invention is illustrated, but in no way limited by the following examples, with reference to the enclosed figures in which.

GENERAL PROCEDURE

X-Ray Powder Diffraction Method Description

Figure 1:
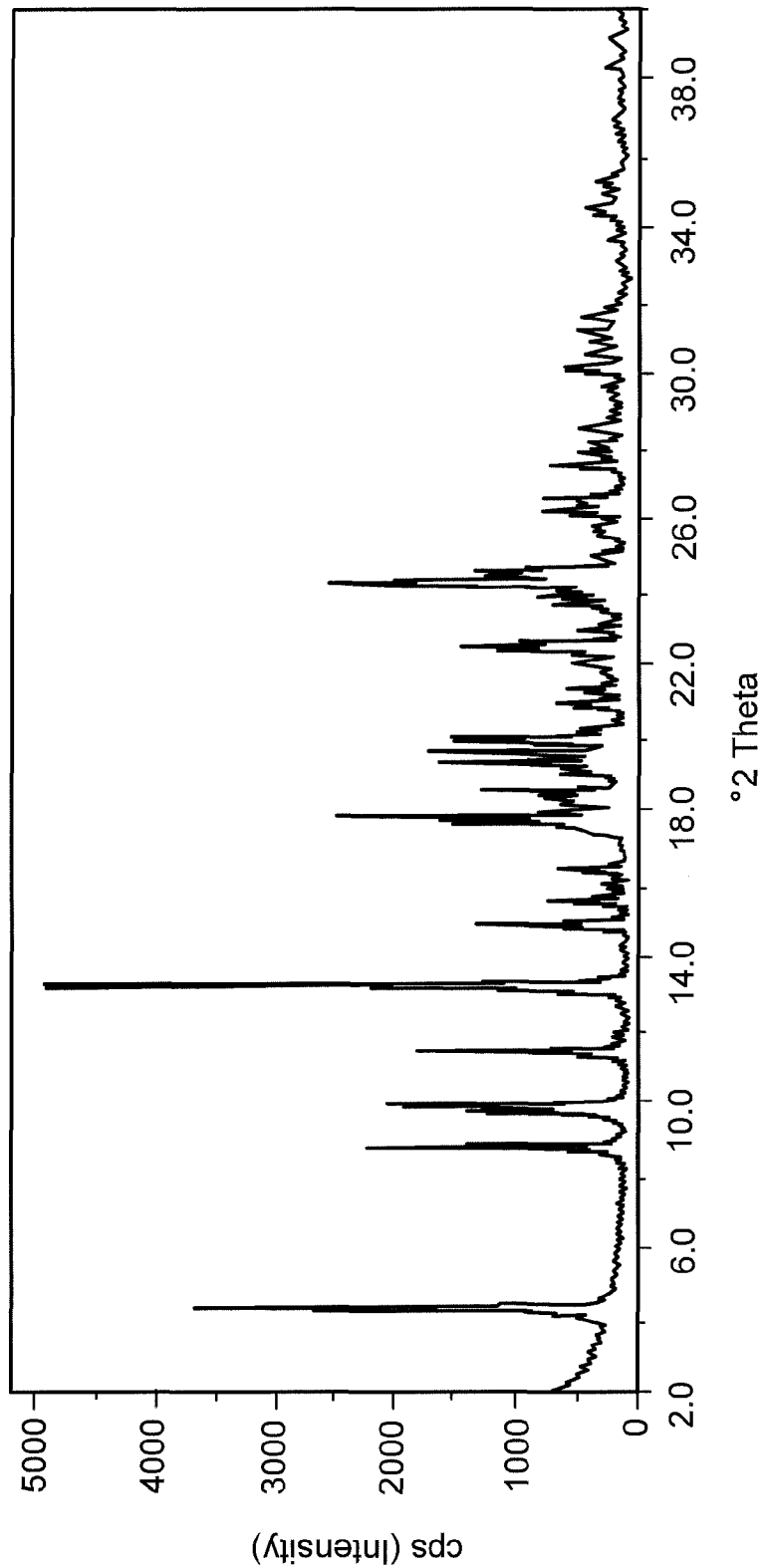
FIG. 1 shows an X-ray powder diffractogram for the crystalline form of Compound I anhydrate, using X-rays of wavelength 1.5418 Å, obtained by way of Example 1 (cps (intensity) values are plotted against ° 2-Theta values).

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the Forms A and D of the present invention are not limited to the crystals that provide X-ray powder diffraction patterns identical to the X-ray powder diffraction pattern shown in FIGS. 1 and 2, and any crystals providing X-ray powder diffraction patterns substantially the same as those shown in FIGS. 1 and 2 fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Generally, a measurement error of a diffraction angle in an X-ray powder diffractogram is about 5% or less, in particular plus or minus 0.5° 2-theta. Typically plus or minus 0.2° 2-theta. Such degree of a measurement error should be taken into account when considering the X-ray powder diffraction patterns in FIGS. 1 and 2 and when reading Tables 1, 2 and 2A. Furthermore, it should be understood that intensities might fluctuate depending on experimental conditions and sample preparation (preferred orientation).

X-ray powder diffraction (XRPD) analysis was performed on samples prepared according to standard methods, for example those described in Giacovazzo, C. et al (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London; or Klug, H. P. & Alexander, L. E. (1974), X-ray Diffraction Procedures, John Wiley and Sons, New York.

X-ray diffraction analyses were performed using a Thermo ARL X'TRA (wavelength of X-rays 1.5418 Å, Cu source, Voltage 45 kV, filament emission 44 mA) for 152 minutes from 2 to 40°. Calculation of peak positions (°2-theta) was done and they may vary in the range ±0.5° 2-theta. However, the data presented in Table 2A on Form D was obtained using a Bruker D4 machine and a wavelength of 1.5418 Å.

It will be appreciated by a skilled person in the art that XRPD intensities may vary when measured for essentially the same crystalline form, for example, preferred orientation.

Differential Scanning Calorimetry

Analytical Instrument: TA Instruments Q1000 DSC. Typically less than 5 mg of material contained in a 40 μl aluminium pan fitted with a lid was heated over the temperature range 25° C. to 300° C. at a constant heating rate of 10° C. per minute. A purge gas using nitrogen was used - flow rate 100 ml per minute.

REFERENCE EXAMPLE 1

(R)-1-(S)-2,2-Dimethyl-1,3-dioxolan-4-yl)ethanol

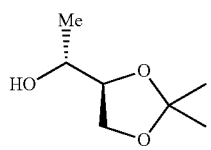

i) 5,6-O-Isopropylidene-L-ascorbic Acid

To a mixture of L-ascorbic acid (65 kg, 369 mol), acetone (283 kg) and 2,2-dimethoxypropane (46 kg, 443 mol) was charged p-toluenesulfonic acid (1.1 kg, 5.5 mol). Temperature was adjusted to 25±5° C. The slurry was stirred for 2 hours, during which time nitrogen was frequently flushed through the bottom valve to prevent material from settling at the bottom of the reactor. NMR analysis (solvent: $D_2O$) then showed 98.5% conversion.

Heptanes (222 kg) were charged and the temperature adjusted to 5±5° C. The reaction mixture was stirred for at least 30 minutes before filtering. Remains of the acetonide product in the reactor were rinsed onto the filter cake using the mother liquors. The filter cake was washed with heptanes (111 kg) and dried at 50° C. to give 5,6-O-isopropylidene-L-ascorbic acid (73 kg, 336 mol) as an almost white powder. Yield: 91%.

$^1$H NMR (400 MHz, d$_6$-DMSO, with maleic acid and TFA) δ4.71 (d, J=3.0 Hz, 1H), 4.28 (m, 1H), 4.11 (dd, J=7.0, 8.4 Hz, 1H), 3.90 (dd, J=6.3, 8.4 Hz, 1H), 1.27 (s, 6H).

ii) (R)-Methyl 2-((S)-2,2-dimethyl-1,3-dioxolan-4-yl)-2-hydroxyacetate 5,6-O-Isopropylidene-L-ascorbic acid (58.8 kg, 272 mol) was charged to sodium hydroxide solution (27.5 kg, 50%, 340 mol) diluted with water (294 kg). and the temperature was adjusted to 30±5° C. Sodium bicarbonate (57 kg, 680 mol) was charged and the mixture was agitated for 15 minutes before the temperature was increased to 40±5° C. Hydrogen peroxide 35% (55 kg, 562 mol) was added to the mixture at 35-60° C. over a period of more than 60 minutes. The reaction mixture was agitated for two hours before NMR analysis (solvent: D$_2$O) showed <1% residual starting material.

Sodium sulfite (4.2 kg, 33 mol) was charged to the reactor and after stirring for 30 minutes, a test for peroxides was negative.

After charging more sodium bicarbonate (34 kg, 408 mol), the mixture was heated to 70±5° C. and agitated for at least one hour before NMR analysis (solvent: D$_2$O) showed 98.5% conversion to the next intermediate, (2R)-[(4S)-2,2-dimethyl-1,3-dioxolan-4-yl](hydroxy)ethanoic acid.

Approximately 150 L of water was stripped off under reduced pressure before filtering off salts. The filter cake was washed with water (30 L).

NMP (330 kg) was charged to the combined mother liquors/wash and the temperature was adjusted to 30±5° C. Methyl iodide (83 kg, 585 mol) was charged and the reactor closed. The temperature was adjusted to 55±5° C. and the reaction mixture was left to react for at least 120 minutes before NMR analysis (solvent: D$_2$O) showed 6% of the residual hydroxy ethanoic acid intermediate.

Sodium sulfite (56 kg, 446 mol) dissolved in water (147 kg) was charged and the mixture was agitated for 30 minutes. The solution was extracted four times for 10 minutes at 30±10° C. using 406 kg toluene in each extraction. The combined organic phase was concentrated by stripping off solvent, under reduced pressure and a maximum temperature of 70° C., until a residual volume of approximately 350 L was reached. The solution was cooled to below 30° C. and transferred to steel barrels over a Millipore filter to give (R)-methyl 2-((S)-2,2-dimethyl-1,3-dioxolan-4-yl)-2-hydroxyacetate solution in toluene (359 kg, 9.4%, 177 mol). Yield: 65%.

$^1$H NMR consistent with commercially available sample of the sub-title product.

iii) (R)-Methyl 2-((S)-2,2-dimethyl-1,3-dioxolan-4-yl)-2-(tosyloxy)acetate

From (R)-Methyl 2-((S)-2,2-dimethyl-1,3-dioxolan-4-yl)-2-hydroxyacetate solution in toluene (359 kg, 9.4%, 177 mol), toluene was distilled off under reduced pressure and a maximum temperature of 70° C. until condensation ceased.

Acetonitrile (153 kg) was charged and the temperature was adjusted to 25±5° C. Triethylamine (41 kg, 405 mol), 4-(dimethyl amino)pyridine (1.12 kg, 9.2 mol) and then, over about 30 minutes, a solution of p-toluenesulfonyl chloride (52.5 kg, 276 mol) in acetonitrile (146 kg) were added at 25±5° C. After stirring the reaction mixture for an additional three hours, NMR analysis (solvent: d$_6$-DMSO) showed acceptable conversion (94%).

MTBE (235 kg) and water (326 kg) were charged and the two-phase system was agitated for about 3 hours, after which time HPLC analysis showed the level of p-toluenesulfonyl chloride to be <0.1% of total peak area. The temperature was adjusted to 25±5° C. and then allowed to separate for 15 minutes. The aqueous phase was taken and extracted with further MTBE (156 kg) before discarding. The 2 organic phases were pooled together and washed with water (326 kg). Then the organic phase was washed 4 times with sodium chloride (16 kg each portion) solution in water (140 kg each portion), each for 5-10 minutes at 25±5° C. Then the organic phase was washed twice with water (185 kg per portion) each for 5-10 minutes at 25±5° C. NMR analysis (solvent: d$_6$-DMSO) then showed <2% NMP (residual from the starting solution), by moles relative to the sulfonate ester intermediate.

Activated carbon (6.0 kg) was charged and the slurry was agitated for 15 minutes at 25±5° C. before the carbon was filtered off in two parallel bag filter. A cartridge filter of 0.6 μm was used after the bag filters. The filters and pipes were rinsed with MTBE (27 kg).

The mother liquors and rinse were combined and reduced in volume by stripping off solvent, under reduced pressure and a maximum temperature of 50° C., until condensation ceased. Heptanes (106 kg) was charged and the solution was reduced once again by stripping off solvent, under reduced pressure and a maximum temperature of 50° C., until condensation ceased, leaving about 60 L solution in the reactor. MTBE (185 kg) was charged followed, after adjusting the temperature to 25±5° C., by heptanes (75 kg). The solution was cooled to 0-5° C. over no less than 30 minutes and heptanes (150 kg) was added over an additional 20 minutes. The slurry was agitated for one hour at 0-5° C. and then filtered. The filter cake was washed with a mixture of MTBE (16 kg) and heptanes (30 kg). The wet product was charged to a vacuum tray dryer and dried at 35° C. (at less than 100 mbar), to give (R)-methyl 2-((S)-2,2-dimethyl-1,3-dioxolan-4-yl)-2-(tosyloxy)acetate (51.3 kg, 154 mol) as a light brown powder. Yield: 87%.

$^1$H NMR (400 MHz, CDCL$_3$) δ7.83 (m, 2H), 7.35 (m, 2H), 4.84 (d, J=4.8 Hz, 1H), 4.46 (m, 1H), 4.04 (dd, J=6.6, 9.1 Hz, 1H), 3.97 (dd, J=5.2, 9.1 Hz, 1H), 3.70 (s, 3H), 2.45 (s, 3H), 1.30 (s, 3H), 1.29 (s, 3H).

iv) (S)-2,2-Dimethyl-4-((R)-oxiran-2-yl)-1,3-dioxolane (R)-Methyl 2-((S)-2,2-dimethyl-1,3-dioxolan-4-yl)-2-(tosyloxy)acetate (76.1 kg, 221 mol) was dissolved in methanol (57 kg) and dichloromethane (208 kg).

Methanol (14 kg), dichloromethane (53 kg) and one-third of the starting material solution (74 mol) were charged to the reactor. The solution was tempered to 10-15° C. Then, sodium borohydride (6.3 kg, 169 mol) was charged in 18 portions to the reactor holding the temperature 8-15° C. The mixture was stirred for half an hour after complete addition. The next one-third of the starting material solution (74 mol), and more sodium borohydride (6.3 kg, 169 mol) were charged, followed by a half-hour stir, using the same procedure as before. This procedure was again repeated with the final one-third of the starting material solution (74 mol) and more sodium borohydride (6.3 kg, 169 mol). HPLC analysis then showed >99.9% conversion to the intermediate (S)-1-((S)-2,2-dimethyl-1,3-dioxolan-4-yl)-2-hydroxyethyl 4-methylbenzenesulfonate.

Dichloromethane (200 kg) was charged to the reaction mixture. Sodium methoxide solution in methanol (43 kg, 30%, 239 mol) was dosed at 20-25° C. for 60 minutes. After approximately half an hour, HPLC analysis showed 99.7% consumption of the intermediate alcohol.

A solution of sodium acetate (25 kg) in water (230 L) was charged to the reaction mixture. The mixture was stirred for 10-15 minutes at 20-25° C. After separation for 15 minutes the lower organic phase was removed. The upper aqueous phase was extracted with dichloromethane (376 kg). The lower organic phase was removed, combining with the first organic phase, and the aqueous phase was discarded.

Water (359 L) was charged to the combined organic phases. After stirring for 10-15 minutes at 20-25° C. and settling for 15 minutes, the lower organic phase was transferred to a reactor containing sodium sulphate (63 kg).

The volume of the mixture was reduced to 310 L by stripping off solvent, and then the sodium sulphate was filtered off. The filter cake was washed with dichloromethane (94 kg). The combined liquors were thoroughly mixed and then discharged to steel drums via a polypropylene bag filter to give (S)-2,2-dimethyl-4-((R)-oxiran-2-yl)-1,3-dioxolane solution in DCM (467.5 kg, 6.2%, 203 mol) as a clear yellow liquid. Yield: 91%.

A sample, free from solvents, may be isolated on a small scale by evaporation of solvent and then distilling under vacuum.

$^1$H NMR (isolated sample, 400 MHz, $d_6$-DMSO) δ4.01 (dd, J=6.6, 8.2 Hz, 1H), 3.92 (m, 1H), 3.72 (dd, J=5.8, 8.2 Hz, 1H), 3.03 (ddd, J=2.6, 4.1, 5.2 Hz, 1H), 2.77 (dd, J=4.1, 5.0 Hz, 1H), 2.58 (dd, J=2.6, 5.0 Hz, 1H), 1.34 (s, 3H), 1.27 (s, 3H).

v) (R)-1-(S)-2,2-Dimethyl-1,3-dioxolan-4-yl)ethanol

From (S)-2,2-Dimethyl-4((R)-oxiran-2-yl)-1,3-dioxolane solution in dichloromethane (465 kg, 6.2%, 200 mol), dichloromethane was distilled at 41-42° C. and replaced by THF (129 kg). Distillation was continued at 60° C. until a set volume in the reactor was reached (235 L). Lithium aluminium hydride (LAH) solution in THF (26.4 kg, 10%, 70 mol) was dosed to the reactor at 22° C. and after subsequent stirring at 25° C. for approximately one hour, GC analysis showed >99.9% consumption of the starting material.

Small portions of water were added via a charging funnel at a rate which was adjusted to control temperature and foaming. A total of 2.6 liters of water (1 L per kg LAH) was added. Sodium hydroxide solution (2.6 kg, 15%, 1 L per kg LAH) was added in the same manner as described for water. Water (7.9 L, 3 L per kg LAH) was charged once more via the charging funnel using the same procedure as before.

The slurry was filtered and the filter cake was washed with THF (36 kg). The filtrate was concentrated by stripping off THF, at a maximum temperature of 85° C., until condensation ceased. 2-MeTHF (129 kg) was charged to the reactor, and then solvent was distilled off to reach a solution volume of approximately 120 L. KF analysis showed <0.1% water. The solution was discharged via a cartridge filter to a PE-lined drum to give (R)-1-((S)-2,2-dimethyl-1,3-dioxolan-4-yl) ethanol solution (103 kg, 27%, 187 mol) as a clear, light yellow liquid. Yield: 94%.

A sample, free from solvents, may be isolated on a small scale by evaporation of solvent and then distilling under vacuum.

$^1$H NMR (isolated sample, 400 MHz, $d_6$-DMSO) δ ppm 4.77 (d, J=5.1 Hz, 1H), 3.95 (dd, J=8.0, 6.2 Hz, 1H), 3.76 (dd, 8.0, 6.0 Hz, 1H), 3.70 (m, 1H), 3.46 (m, 1H), 1.29 (s, 3H), 1.25 (s, 3H), 1.07 (d, J=6.2 Hz, 3H).

EXAMPLE 1

Form A—Compound I Anhydrate

Compound I, i.e. N-[2-[[(2,3-difluorophenyl)methyl]thio]-6-{[(1R,2S)-2,3-dihydroxy-1-methylpropyl]oxy}-4-pyrimidinyl]-1-azetidinesulfonamide (for instance, as prepared in accordance with Example 47 in WO 2006/024823) is used in the following procedure.

1. Charge Compound I MAPI (43.94 g, 100% mass=40.0 g) and acetonitrile (160 mL, 4.0 rel vols) to vessel 1 and stir at 20° C.
2. Screen the mixture into vessel 2 and rinse vessel 1 and the lines with acetonitrile (20 mL, 0.50 rel vols). Stir, and heat to 55° C.
   Whatman grade 3 filter papers (6μm pore size, 32 mm diameter circular filter area) were used.
   The filter paper may be swapped for a fresh one (if filtration using suction slows down).
   After the filtration, the solution was weighed and found to be a smaller than expected mass. It was topped up with a small charge of acetonitrile (10 mL, 0.25 rel vols), to correct for the evident losses to evaporation.
3. Charge phosphoric acid (8.80 g, 0.22 rel wt) followed by water (20 mL, 0.50 rel vols) to the stirring vessel 2 solution and change the set point to 51° C.
   The acid and water may be charged together if this is more convenient.
4. Sample the reaction to determine conversion after 10 and 35 minutes.
   It is important to dilute the samples for the HPLC analysis as soon as possible after taking them, noting the time at which the dilutions were actually made.
   Conversion was 45, 81 and 93% after 10.5, 32 and 57 mins, respectively. Moved on to step 5 at t=135 mins.
5. Heat to 71° C.
   Step 6 should be started as soon as possible after reaching around 68° C.
6. Charge water (204 mL, 5.1 rel vols), slowly enough to maintain the temperature above 67° C.
7. Cool to 65° C.
   It is important that the reaction temperature be as close as possible to the set point before proceeding. 2-3° C. below may result in very rapid crystallisation and associated problems. 3° C. higher may go above the clear point and from there crystallisation cannot be started.
8. If necessary, generate a seed for crystallisation by diluting a sample of the solution (0.48 mL, 0.012 rel vols) with water (1.44 mL, 0.036 rel vols). Mix well and then charge the slurry back into the solution.
9. Hold at 65° C. for 40 mins.
10. Cool by 6° C. at a rate of 3° C./hr (65-59° C. over 2.0 hours), then by 8° C. at 4° C./hr (59-51° C.) and finally to 20° C. at 6° C./hr (51-20° C. over 5.2 hrs).
11. Check that the crystallisation has reached a suitable equilibrium.
12. Filter, wash the cake twice with 3:2 water:acetonitrile v:v (2×120 mL, 2×3.00 rel vols), incorporating a rinse of vessel 2 for each wash, and then dry at 60° C. to constant mass.

Alternatively, Form A may be prepared as follows:

1. Charge N-[2-[[(2,3-difluorophenyl)methyl]thio]-6-[(1R)-1-[(4S)-2,2-dimethyl-1,3-dioxolan-4-yl]ethoxy]-4-pyrimidinyl]-1-azetidinesulfonamide (for instance, as prepared in accordance with Example 47 in WO 2006/024823) (43.94 g, 100% mass=40.0 g) and acetonitrile (160 mL, 4.0 rel vols) to vessel 1 and stir at 20° C.

2. Screen the mixture into vessel 2 and rinse vessel 1 and the lines with acetonitrile (20 mL, 0.50 rel vols). Stir, and heat to 55° C.
   Whatman grade 3 filter papers (6 μm pore size, 32 mm diameter circular filter area) were used.
   The filter paper may be swapped for a fresh one (if filtration using suction slows down).
   After the filtration, the solution was weighed and found to be a smaller than expected mass. It was topped up with a small charge of acetonitrile (10 mL, 0.25 rel vols), to correct for the evident losses to evaporation.
3. Charge phosphoric acid (8.80 g, 0.22 rel wt) followed by water (20 mL, 0.50 rel vols) to the stirring vessel 2 solution and change the set point to 51° C.
   The acid and water may be charged together if this is more convenient.
4. Sample the reaction to determine conversion after 10 and 35 minutes.
   It is important to dilute the samples for the HPLC analysis as soon as possible after taking them, noting the time at which the dilutions were actually made.
   Conversion was 45, 81 and 93% after 10.5, 32 and 57 mins, respectively. Moved on to step 5 at t=135 mins.
5. Heat to 71° C.
   Step 6 should be started as soon as possible after reaching around 68° C.
6. Charge water (204 mL, 5.1 rel vols), slowly enough to maintain the temperature above 67° C.
7. Cool to 65° C.
   It is important that the reaction temperature be as close as possible to the set point before proceeding. 2-3° C. below may result in very rapid crystallisation and associated problems. 3° C. higher may go above the clear point and from there crystallisation cannot be started.
8. Hold at 65° C. for 40 mins.
9. Cool by 6° C. at a rate of 3° C./hr (65-59° C. over 2.0 hours), then by 8° C. at 4° C./hr (59-51° C.) and finally to 20° C. at 6° C./hr (51-20° C. over 5.2 hrs).
10. Check that the crystallisation has reached a suitable equilibrium.
11. Filter, wash the cake twice with 3:2 water:acetonitrile v:v (2×120 mL, 2×3.00 rel vols), incorporating a rinse of vessel 2 for each wash, and then dry at 60° C. to constant mass to give Compound 1 as Form A.
    Alternatively, form A may be prepared by dissolving N-[2-[[(2,3-difluorophenyl)methyl]thio]-6-{[(1R,2S)-2,3-dihydroxy-1-methylpropyl]oxy}-4-pyrimidinyl]-1-azetidinesulfonamide (as prepared from N-[2-[[(2,3-difluorophenyl)methyl]thio]-6-[(1R)-1-[(4S)-2,2-dimethyl-1,3-dioxolan-4-yl]ethoxyl]-4-pyrimidinyl]-1-azetidinesulfonamide in accordance with Example 47 in WO 2006/024823) in water (6.2 relative volumes) and acetonitrile (5 relative volumes) by heating to 70° C. Once this temperature is reached and the solution is clear, the solution is slowly cooled to 20° C. Crystallisation normally commences at a temperature close to 60° C. to give Form A.
    The XRPD pattern of Form A using a wavelength of 1.5418 Å on a Thermo ARL X'TRA XRD machine is shown in FIG. 1 and is tabulated in Table 1 below.

TABLE 1

| Angle (2-Theta °) | Relative Intensity (%) |
|---|---|
| 4.4 | vs |
| 8.7 | vs |
| 9.7 | s |

TABLE 1-continued

| Angle (2-Theta °) | Relative Intensity (%) |
|---|---|
| 9.9 | vs |
| 11.4 | vs |
| 13.1 | vs |
| 14.8 | s |
| 15.5 | s |
| 15.9 | m |
| 16.3 | s |
| 17.6 | vs |
| 17.8 | vs |
| 18.2 | s |
| 18.5 | s |
| 19.0 | m |
| 19.2 | vs |
| 19.5 | vs |
| 19.9 | vs |
| 20.1 | m |
| 21.9 | m |
| 22.4 | vs |
| 23.8 | s |
| 24.1 | vs |
| 24.4 | s |
| 24.9 | m |
| 26.1 | s |
| 26.5 | s | approx. 25-100% = "vs", approx. 10-25% = "s", approx. 3-10% = "m" and approx. 1-3% = "w"

This anhydrate form of Compound I was highly crystalline.

EXAMPLE 2

Form D—Compound I Anhydrate

Form A of Compound I as obtained for instance by the process described in Example 1 above was converted to Form D.

Form A of Compound I was slurried in methanol at 50° C. for 6 weeks to obtain the D-form.

It may also be possible to obtain the D form by slurrying the product of Example 47 in WO 2006/024823 in methanol at 50° C. for 6 weeks.

Figure 3:
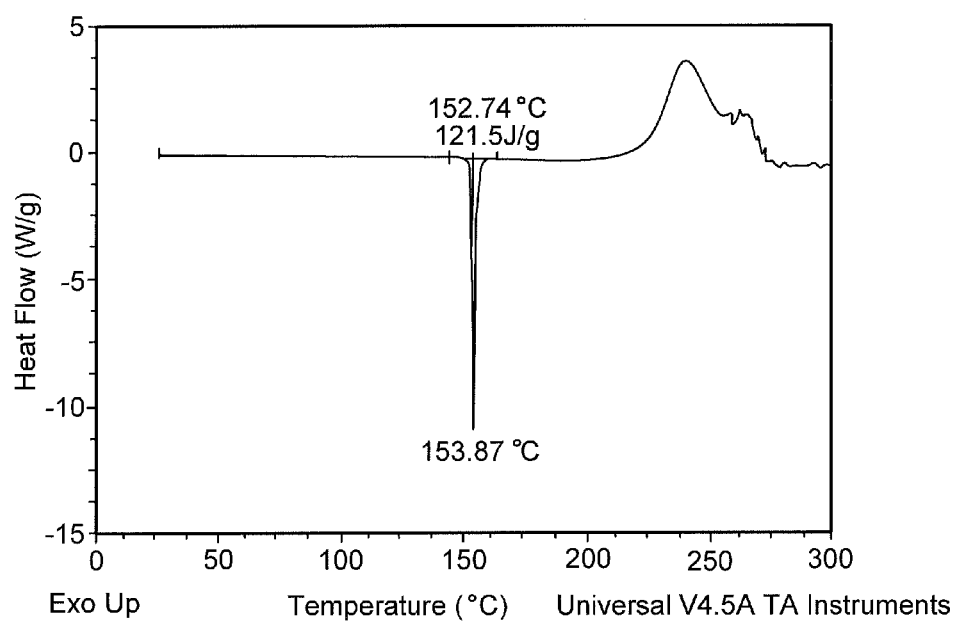
FIG. 3 shows DSC for the crystalline form of Compound I anhydrate obtained by way of Example 2.

Using DSC, form D had a melting point of 152.7° C. (onset). See FIG. 3 below.

Figure 2:
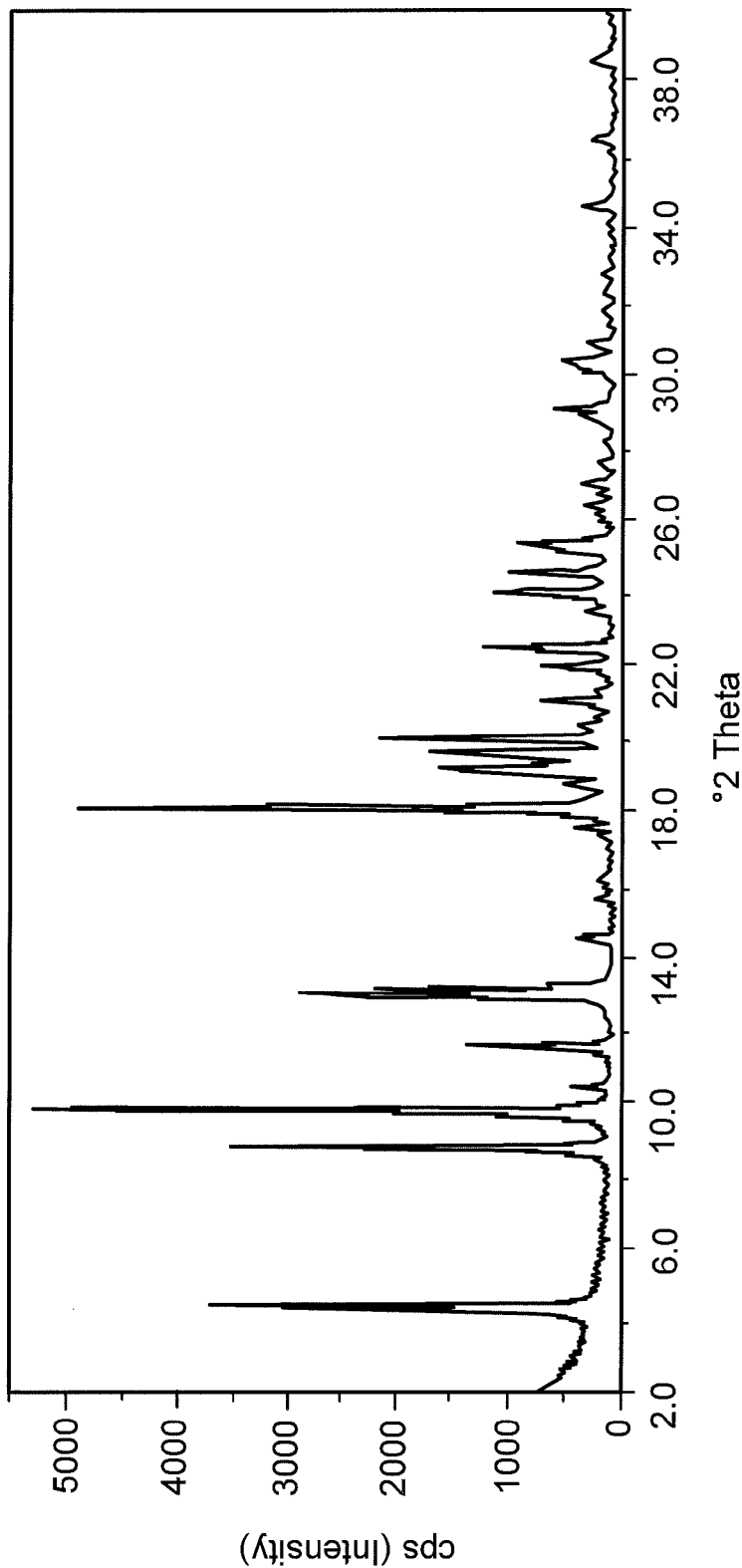
FIG. 2 shows an X-ray powder diffractogram for the crystalline form of Compound I anhydrate, using X-rays of wavelength 1.5418 Å, obtained by way of Example 2 (cps (intensity) values are plotted against ° 2-Theta values).

The XRPD pattern of the form D using a wavelength of 1.5418 Å on a Thermo ARL X'TRA XRD machine is shown in FIG. 2 and is tabulated in Table 2 below.

TABLE 2

| Angle (2-Theta °) | Relative Intensity (%) |
|---|---|
| 4.4 | vs |
| 8.7 | vs |
| 9.7 | vs |
| 11.5 | s |
| 12.9 | vs |
| 13.1 | vs |
| 14.5 | s |
| 18.0 | vs |
| 19.0 | vs |
| 19.1 | vs |
| 19.3 | s |
| 19.5 | s |
| 19.9 | vs |
| 21.0 | s |
| 21.9 | s |
| 22.5 | vs |
| 23.9 | s |
| 24.5 | s |
| 25.1 | s |
| 25.3 | s |
| 27.0 | s |

TABLE 2-continued

| Angle (2-Theta °) | Relative Intensity (%) |
|---|---|
| 28.6 | m |
| 28.8 | s |
| 29.1 | s |
| 30.4 | s |
| 34.6 | m |
| 36.4 | m | approx. 25-100% = "vs", approx. 10-25% = "s", approx. 3-10% = "m" and approx. 1-3% = "w"

The XRPD pattern of the form obtained by way of Example 1 using a wavelength of 1,5418 Å on a Bruker D4 XRD machine is tabulated in Table 2A below.

TABLE 2A

| D value | 2-Theta ° | % |
|---|---|---|
| d = 20.009 | 4.4 | 85.3 |
| d = 10.068 | 8.8 | 100.0 |
| d = 9.029 | 9.8 | 73.9 |
| d = 8.428 | 10.5 | 12.4 |
| d = 7.630 | 11.6 | 23.4 |
| d = 6.822 | 13.0 | 58.5 |
| d = 6.725 | 13.2 | 68.4 |
| d = 6.088 | 14.5 | 11.8 |
| d = 5.647 | 15.7 | 12.9 |
| d = 5.493 | 16.1 | 11.4 |
| d = 5.048 | 17.6 | 14.7 |
| d = 4.899 | 18.1 | 94.3 |
| d = 4.731 | 18.7 | 17.0 |
| d = 4.647 | 19.1 | 27.9 |
| d = 4.614 | 19.2 | 27.7 |
| d = 4.577 | 19.4 | 26.5 |
| d = 4.527 | 19.6 | 31.0 |
| d = 4.434 | 20.0 | 55.3 |
| d = 4.356 | 20.4 | 19.2 |
| d = 4.305 | 20.6 | 14.8 |
| d = 4.219 | 21.0 | 14.9 |
| d = 4.155 | 21.4 | 13.1 |
| d = 4.049 | 21.9 | 24.4 |
| d = 4.039 | 22.0 | 26.5 |
| d = 3.942 | 22.5 | 51.0 |
| d = 3.781 | 23.5 | 16.3 |
| d = 3.706 | 24.0 | 38.4 |
| d = 3.618 | 24.6 | 23.4 |
| d = 3.529 | 25.2 | 33.0 |
| d = 3.506 | 25.4 | 38.2 |
| d = 3.421 | 26.0 | 8.5 |
| d = 3.368 | 26.4 | 16.4 |
| d = 3.297 | 27.0 | 14.1 |
| d = 3.109 | 28.7 | 9.7 |
| d = 3.090 | 28.9 | 16.2 |
| d = 3.064 | 29.1 | 18.4 |
| d = 2.962 | 30.1 | 12.9 |
| d = 2.933 | 30.4 | 24.8 |
| d = 2.889 | 30.9 | 11.6 |
| d = 2.770 | 32.3 | 9.1 |
| d = 2.728 | 32.8 | 8.4 |
| d = 2.638 | 34.0 | 8.5 |
| d = 2.588 | 34.6 | 15.2 |
| d = 2.461 | 36.5 | 10.9 |
| d = 2.363 | 38.0 | 6.0 |
| d = 2.329 | 38.6 | 11.6 |

This anhydrate form of Compound I was also highly crystalline and was also more thermodynamically stable than the A-form obtained by means of Example 1 (see Example 3 below).

EXAMPLE 3

Form D—Compound I Anhydrate

Modification D can be generated using an anti-solvent crystallization utilizing ethanol as the solvent and water as the anti-solvent.

An 80% saturated solution of the compound is prepared in ethanol, for example by dissolving 1 relative weight of the compound in 83 relative volumes of ethanol at a temperature of 25° C. (equivalent to 12 mg of AZD 5069 in 1 mL of ethanol). The solution can be prepared from crystalline material of form A or from amorphous material. To this solution 166 relative volumes of water (i.e. twice the volume of water with respect to the ethanol) are added, either continuously over a period of time or in several aliquots. Upon addition of water the compound crystallizes as modification D and can be isolated by filtration from the slurry.

EXAMPLE 4

Form D—Compound I Anhydrate (Seeding Method)

Form D was also prepared in 80% yield by a seeding method, which involved dissolving Compound I (e.g. one relative 'weight') in a solvent (such as an alcohol, e.g. isopropanol; e.g. 30 relative volumes or ethanol; 15 relative volumes); stirring at elevated temperature (e.g. 70° C.) for instance for a period of time (which may be several hours) to achieve full dissolution; continuing stirring at elevated temperature (e.g. 55° C.; i.e. a temperature lower than that required to achieve dissolution) for several hours (e.g. overnight); seeding with Form D of Compound I (e.g. 0.1 weight %); cooling to a lower temperature (e.g. 20° C.); and filtering.

EXAMPLE 5

Thermodynamic Stability

Competitive slurry trials were performed between the A-form (obtained by Example 1) and the D-form (obtained by Example 2).

Competitive slurries containing the A-form and D-form in methanol were held at any temperatures ranging from about 5° C. to about 50° C. It was found that the D-form remained stable under these conditions. However, the A-form transforms to the D-form.

Complete conversion of the A-form to the D-form takes place, if the slurry is held at a particular temperature for a sufficient duration of time.

This shows that the D-form is a thermodynamically more stable form than the A-form, at least in the relevant particular temperature range, and hence the D-form may be even more advantageous than the A-form for use as a medicament.

The invention claimed is:

1. A crystalline form of N-[2-[[(2,3-difluorophenyl)methyl]thio]-6-{[(1R,2S)-2,3-dihydroxy-1-methylpropyl]oxy}-4-pyrimidinyl]-1-azetidinesulfonamide, characterised by a powder X-ray diffraction pattern, measured using a wavelength of X-rays 1.5418 Å, comprising at least one crystalline peak with a 2-Theta value (in degrees) selected from 21.0, 28.8 and 29.1.

2. The crystalline form as claimed in claim 1 characterised by a powder X-ray diffraction pattern, measured using a wavelength of X-rays 1.5418 Å, comprising at least 2 crystalline peaks with a 2-Theta value (in degrees) selected from 21.0, 28.8 and 29.1.

3. The crystalline form as claimed in claim 2 characterised by a powder X-ray diffraction pattern, measured using a wavelength of X-rays 1.5418 Å, comprising at least 3 crystalline peaks with a 2-Theta value (in degrees) of 21.0, 28.8 and 29.1.

4. The crystalline form as claimed in claim 1 characterised by a powder X-ray diffraction pattern, measured using a wavelength of X-rays 1.5418 Å, comprising a further crystalline peak with a 2-Theta value (in degrees) selected from of 12.9 and 18.0.

5. The crystalline form as claimed in claim 1 characterised by a powder X-ray diffraction pattern, measured using a wavelength of X-rays 1.5418 Å, comprising crystalline peaks with a 2-Theta value (in degrees) of 12.9, 13.1, 18.0, 21.0, 22.5, 25.1, 25.3, 28.8, 29.1 and 30.4.

6. A crystalline form of N-[2[[(2,3-difluorophenyl)methyl]thio]-6-{[(1R,2S)-2,3-dihydroxy-1-methylpropyl]oxy}-4-pyrimidinyl]-1-azetidinesulfon-amide, characterised by a powder X-ray diffraction pattern, measured using a wavelength of X-rays 1.5418 Å, comprising at least one crystalline peak with a 2-Theta value (in degrees) of around 12.9, 18.0 and/or 21.0.

7. A crystalline form of N-[2[[(2,3-difluorophenyl)methyl]thio]-6-{[(1R,2S)-2,3-dihydroxy-1-methylpropyl]oxy}-4-pyrimidinyl]-1-azetidinesulfon-amide which has a melting point (onset) of 152.7° C.

* * * * *